United States Patent [19]

Williamson, IV et al.

[11] Patent Number: 5,630,541

[45] Date of Patent: May 20, 1997

[54] SURGICAL STAPLER AND STAPLE CARTRIDGE

[75] Inventors: Warren P. Williamson, IV, Loveland; Thomas W. Huitema, Cincinnati; James H. Chambers, Milford, all of Ohio

[73] Assignee: Ethicon Endo-Surgery, Inc., Cincinnati, Ohio

[21] Appl. No.: 360,460

[22] Filed: Dec. 21, 1994

Related U.S. Application Data

[62] Division of Ser. No. 58,325, May 5, 1993, Pat. No. 5,415,334.

[51] Int. Cl.$^6$ .................................................. A61B 17/072
[52] U.S. Cl. ........................... 227/178.1; 227/180.1; 227/19
[58] Field of Search ................... 227/175.1, 176.1, 227/178.1, 180.1, 19

[56] References Cited

U.S. PATENT DOCUMENTS

| | | | |
|---|---|---|---|
| 3,079,606 | 3/1963 | Bobrov et al. | 227/76 |
| 3,252,643 | 5/1966 | Strekopytov et al. | 227/109 |
| 3,490,675 | 1/1970 | Green et al. | 227/19 |
| 3,499,591 | 3/1970 | Green | 227/76 |
| 3,795,034 | 3/1974 | Strekopytov et al. | 227/178.1 |
| 4,305,539 | 12/1981 | Korolkov et al. | 227/19 X |
| 4,402,444 | 9/1983 | Green | 227/19 |
| 4,506,670 | 3/1985 | Crossley | 227/19 X |
| 4,506,671 | 3/1985 | Green | 227/19 X |
| 4,605,001 | 8/1986 | Rothfuss et al. | 227/19 X |
| 4,610,383 | 9/1986 | Rothfuss et al. | 227/19 |
| 4,633,874 | 1/1987 | Chow et al. | 227/19 X |
| 4,715,520 | 12/1987 | Roehr, Jr. et al. | 227/19 |
| 4,767,004 | 8/1988 | Green | 227/19 |
| 4,848,637 | 7/1989 | Pruitt | 227/19 |
| 4,930,503 | 6/1990 | Pruitt | 227/178.1 |
| 4,978,049 | 12/1990 | Green | 227/178.1 |
| 5,180,092 | 1/1993 | Crainich | 227/180.1 |
| 5,413,268 | 5/1995 | Green et al. | 227/176.1 |
| 5,465,896 | 11/1995 | Allen et al. | 227/176.1 |
| 5,482,197 | 1/1996 | Green et al. | 227/178.1 |

*Primary Examiner*—Joseph J. Hail, III
*Assistant Examiner*—Jay A. Stelacone
*Attorney, Agent, or Firm*—Dressler, Goldsmith, Milnamow & Katz, Ltd.

[57] ABSTRACT

A surgical stapler comprising at least one cam having a cam surface, an arrangement for actuating the cam for a longitudinal firing movement of the cam surface, a cartridge having a plurality of staple drive members driven by the longitudinal movement of the cam surface, and a plurality of surgical staples respectively associated with the staple drive members for being fired by the longitudinal movement of the cam surface. In one embodiment of the present invention, the staple drive members include at least a pair of alternating first and second staple drive members, the first staple drive member including a laterally spaced pair of staple driving surfaces, the second staple drive member including a single staple driving surface. The first and second staple drive members are disposed such that the staple driving surfaces thereof are arranged in laterally spaced three rows. Alternate embodiments include drive members each having a pair of longitudinally aligned driving surfaces, and a third laterally offset driving surface, as well as a spine-like flexible drive element operatively positioned between the cam surface of the cam and the drive members.

3 Claims, 8 Drawing Sheets

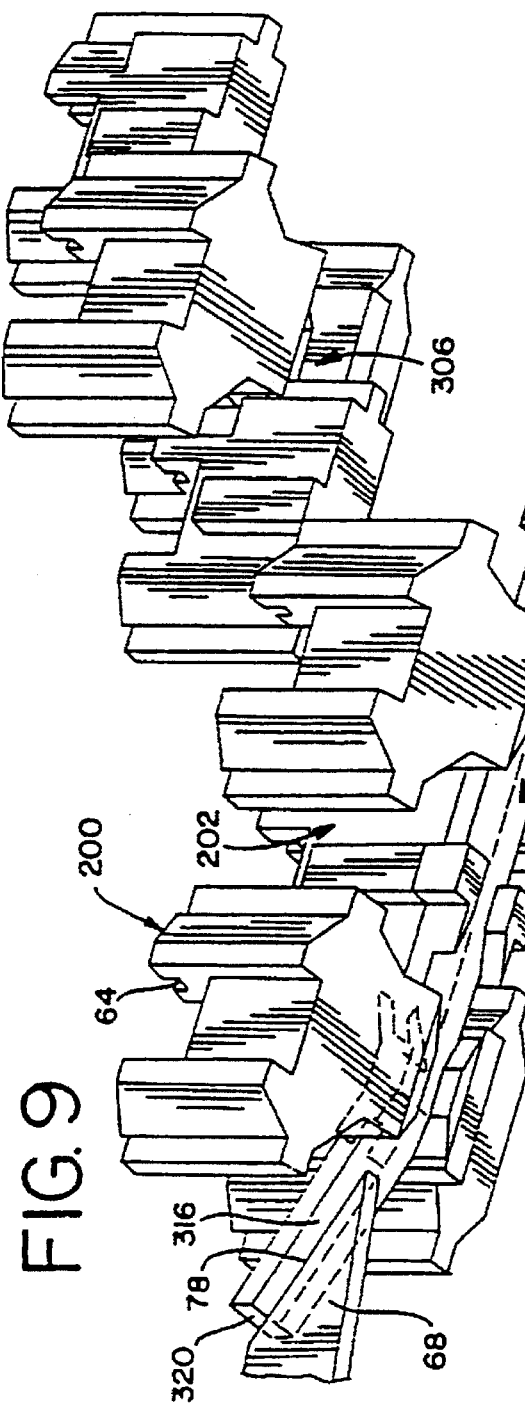
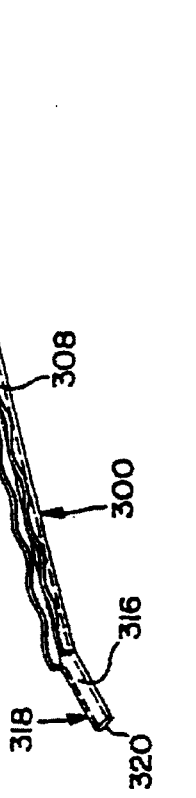
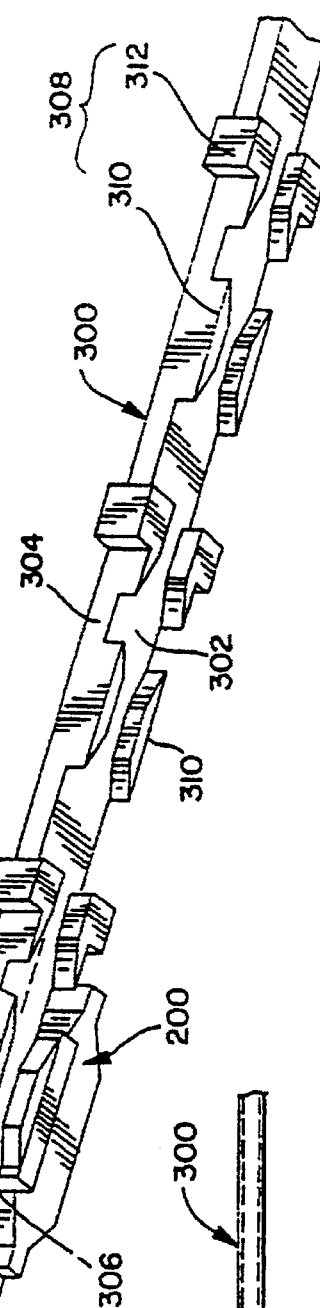
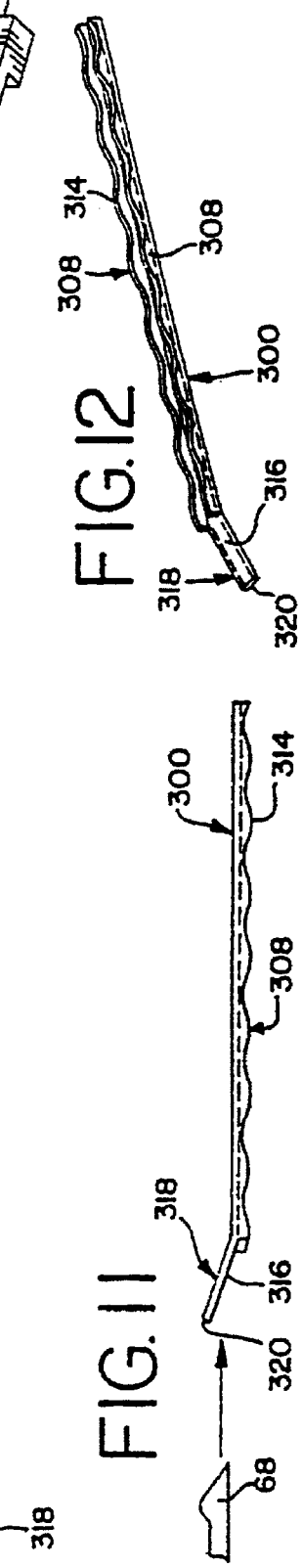

SURGICAL STAPLER AND STAPLE CARTRIDGE

This application is a division of application Ser. No. 08/058,325, filed May 5, 1993 now U.S. Pat. No. 5,415,334.

FIELD OF THE INVENTION

The present invention relates to an improved surgical stapler of the type which includes a staple cartridge having a plurality of staple drive members in association with surgical staples which are designed to be driven by longitudinal movement of cam means for firing the surgical staples into body tissue. The drive members of the present cartridge can be configured to drive three laterally adjacent rows of staples.

BACKGROUND OF THE INVENTION

Surgical staplers have found wide-spread acceptance in surgical procedures since such devices drastically reduce the amount of time required by surgeons to suture body tissue.

Typically, such surgical staplers have a pair of upper and lower jaw members to clamp body tissue therebetween. The lower jaw member typically carries a staple cartridge which contains a plurality of staple drive members having cam contact surfaces in association with one or more laterally spaced rows of surgical staples. The upper jaw member has an anvil portion to close the surgical staples which have passed through body tissue. The stapler is further provided with at least one pusher bar longitudinally moveable relative to the jaw members and having a cam surface for engaging the cam contact surfaces of the staple drive members so that the longitudinal movement of the pusher bar sequentially drives the staple drive members, through a camming action, to fire surgical staples from the cartridge.

For some uses, double-row stapling is preferable to single-row stapling in providing secure hemostasis. Accordingly, some currently available surgical staplers include double staple drive members respectively formed of a single piece construction having two staple driving surfaces for firing two rows of surgical staples. These double staple drive members are longitudinally arranged in a row within the cartridge to be driven with a single stroke of the pusher bar. Typical arrangements include double staple drive members each having a longitudinally-staggered pair of staple driving surfaces which bridge the pusher bar path.

U.S. Pat. No. 4,978,049, to Green, discloses a modification which includes triple staple drive members respectively formed of a single piece construction having three laterally spaced staple driving surfaces capable of firing three rows of surgical staples. However, this arrangement has distinct disadvantages.

As the number of the staple driving surfaces for firing individual staples increases, greater resistance is created to the longitudinal movement of pusher bar. This requires a surgeon to apply a greater force in operating the surgical stapler. Furthermore, there can be a tendency for the staple drive members to bind against the walls of cartridge slots and jam due to an unbalanced force distribution applied to staple driving surfaces.

Therefore, it is highly desirable to design and arrange the pattern of individual staple drive members and driving surfaces to facilitate application of the driving force by the surgeon throughout the pusher bar stroke to provide a surgical stapler which allows a smooth stapling operation.

SUMMARY OF THE INVENTION

A surgical stapler in accordance with the present invention comprises a staple-filled cartridge, cam means having a cam surface movable through the cartridge, means for actuating the cam means for a longitudinal firing movement of the cam surface, a plurality of staple drive members in the cartridge driven by the longitudinal movement of the cam surface, and a plurality of surgical staples respectively associated with the drive members for being fired by the longitudinal movement of the cam surface.

In one embodiment of the present invention, the staple drive members of the staple cartridge include at least a pair of alternating first and second staple drive members arranged in the longitudinal direction. The first staple drive member has a laterally spaced pair of staple driving surfaces respectively in association with the surgical staples. The second staple drive member has a single staple driving surface associated with one of the surgical staples, which driving surface is disposed laterally between the pair of staple driving surfaces of the first staple drive member, so that the laterally spaced pair of driving surfaces of the first staple drive member and the single staple driving surface of the second staple drive member are arranged in three laterally spaced rows along the longitudinal direction.

In the illustrated embodiment of the present invention, the first staple drive member is generally H-shaped to define the laterally spaced pair of staple driving surfaces. The second staple drive member is configured to be complementary to the first H-shaped staple drive member, so that the single staple driving surface of the second staple drive member is flanked by and positioned between the laterally spaced pair of staple driving surfaces of the first staple drive member.

In another embodiment of the present invention, a surgical stapler includes a cartridge having a plurality of staple drive members each having three staple driving surfaces respectively in association with surgical staples. The three staple driving surfaces comprise a pair of front and rear staple driving surfaces aligned in the direction of the longitudinal movement of the cam surface and a center staple driving surface laterally spaced from the front and rear driving surfaces. At least one longitudinally extending cam surface is formed in each of the staple drive members so that it is laterally spaced from the three staple driving surfaces.

Longitudinally adjacent staple drive members are arranged in a laterally inverted or reversed orientation and configured to be complementary to each other, so that the staple driving surfaces of the staple drive members are arranged in three laterally spaced rows and the cam contact surfaces of the staple drive members are arranged in one or more rows laterally spaced from the rows of the staple driving surfaces.

In a particular embodiment, the center staple driving surfaces of the adjacent staple drive members are aligned in the longitudinal direction, so that the staple driving surfaces of the drive members are arranged in three laterally spaced rows. In another embodiment, the center staple driving surface of each of the drive members is longitudinally aligned with the front and rear driving surfaces of its adjacent drive members, so that the staple driving surfaces of the drive members are arranged in two laterally spaced rows.

The present invention further provides a surgical staple driver arrangement which includes a staple cartridge having a plurality of drive members arranged in one or more rows in the direction of the movement of the cam surface, a plurality of surgical staples respectively associated with the drive members and a flexible drive element having a continuous surface extending in the moving direction of movement of the cam surface in operative association with the drive members. The continuous surface of the flexible drive element is associated with the cam means for being engaged by the cam surface, so that the longitudinal movement of the cam surface effects a sequential pushing of the drive members for firing the surgical staples. The flexible nature of the flexible element enables a subsequent, and sequential self-formation of the inclined cam contact surface. Accordingly, the cam surface at minimum needs to continuously advance on the flexible element. This permits a reduced length of the cam surface. Such cam surface may be just a round tip of a pusher bar. The reduced length of the cam surface desirably permits a reduced length of the staple cartridge, which is required to have at its distal end a space for accommodating the cam surface after it moves to the distal-most end of its travel.

At least some of the drive members may be integrally connected to the flexible drive element. In a particular embodiment of the invention, alternate ones of the drive members are integrally connected to the flexible drive element. The continuous surface of the flexible drive element may further include an inclined surface portion for engageably receiving the cam surface of the cam means, and/or a guide surface portion, preferably comprising a projected sleeve surface for guiding the cam surface in the longitudinal direction.

The present invention provides a new and improved surgical stapler which promotes a smooth and effective operation during stapling. Numerous other advantages and features of the present invention will become readily apparent from the following detailed description, the appended drawings, and the accompanying claims.

BRIEF DESCRIPTION OF THE DRAWINGS

FIG. 9 is an partly exploded, perspective view of the flexible drive element and the first and second staple drive members in accordance with the present invention;

FIG. 10 is a bottom view of the flexible drive element;

FIG. 11 is a side elevational view of the flexible drive element, illustrating an inclined ramp contact surface for being engaged by a cam surface of the pusher bar;

FIG. 12 is a perspective view of the flexible drive element, illustrating the inclined ramp contact surface and undulated top surface of each guide ridge formed therein;

DETAILED DESCRIPTION OF PREFERRED EMBODIMENTS

Figure 1:
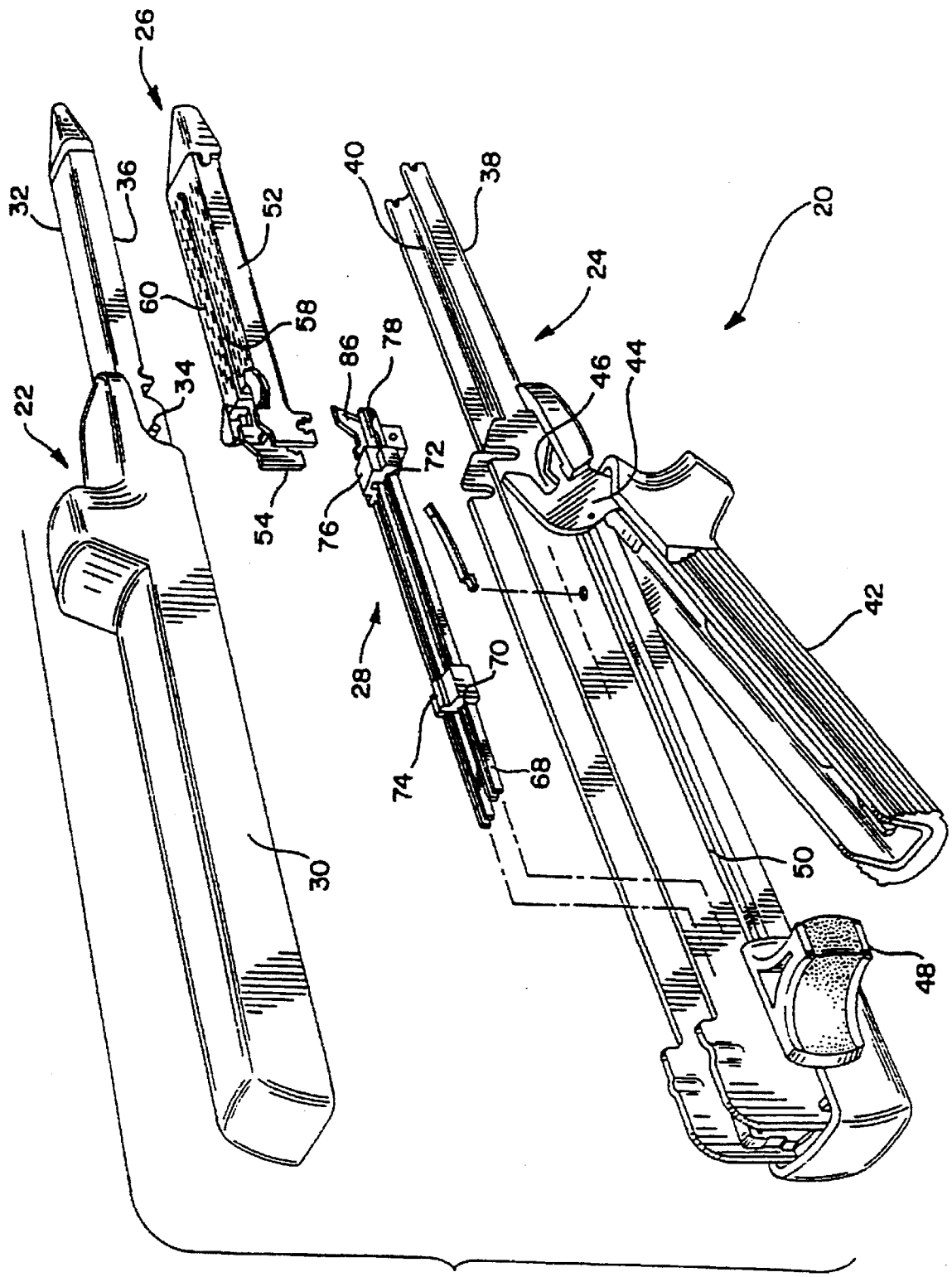
FIG. 1 is an exploded perspective view of a surgical stapler embodying the principles of the present invention.

While the present invention is susceptible of embodiment in various forms, there is shown in the drawings and will hereinafter be described various presently preferred embodiments of the invention, with the understanding that the present disclosure is to be considered as an exemplification of the invention, and is not intended to limit the invention to the specific embodiments illustrated and described herein.

Figure 2:
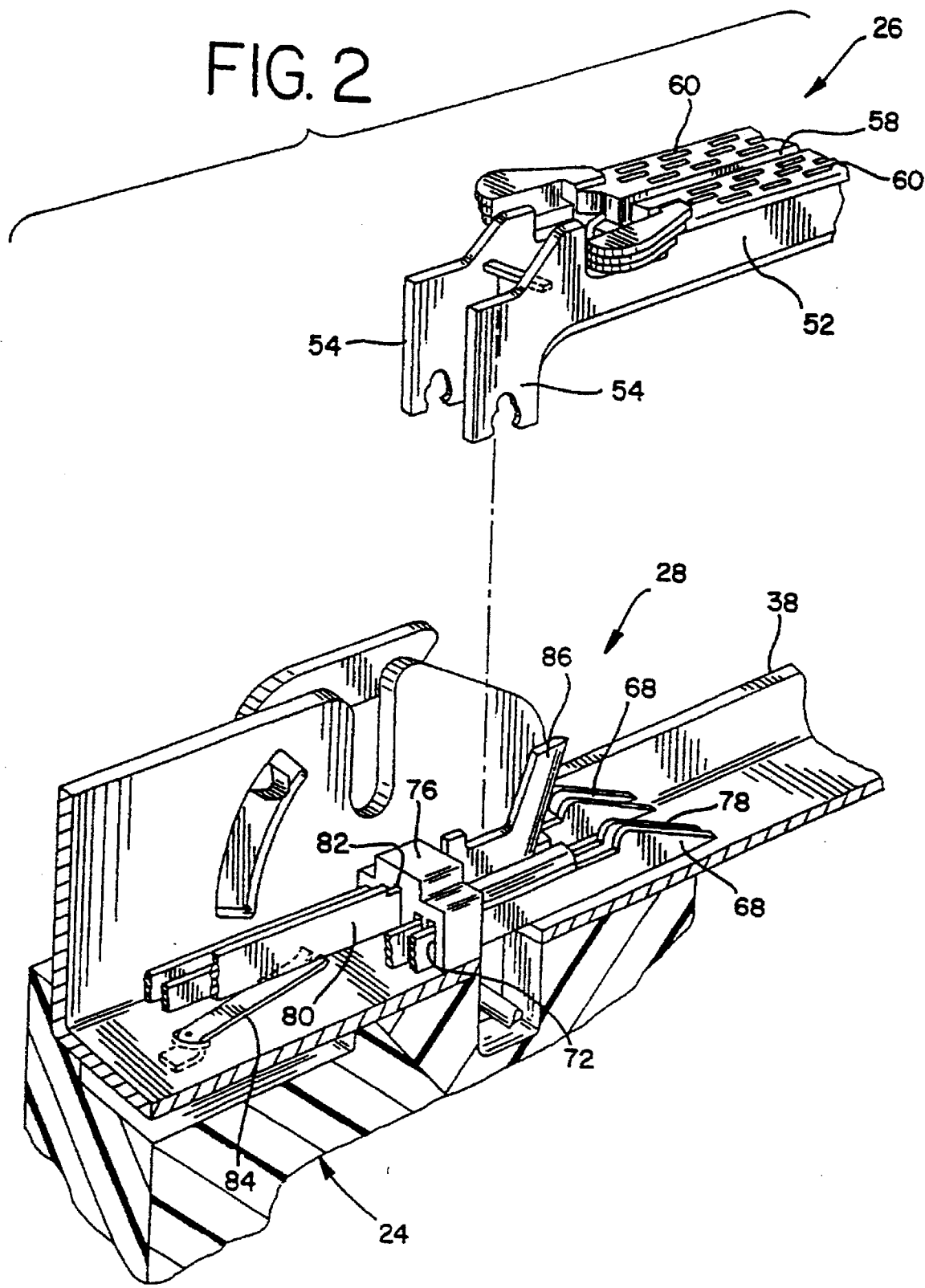
FIG. 2 is an exploded, partly broken away, perspective view of the firing means of the stapler of FIG. 1.
Figure 3:
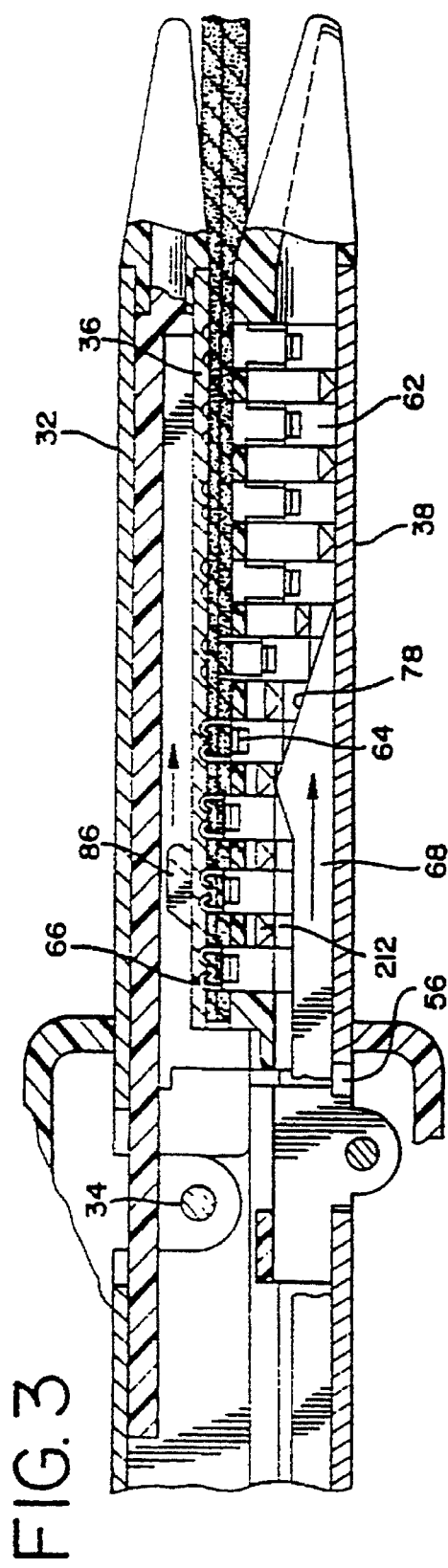
FIG. 3 is an enlarged, partly broken, cross-sectional view of the stapler of FIG. 1 showing the upper jaw portion and the lower jaw portion mounting the staple cartridge, and illustrating stapling operation of the pusher bar and the knife blade.

Referring now to the drawings, therein is illustrated in FIGS. 1 through 3, a typical surgical stapler 20 which generally comprises an upper frame 22, a lower frame 24, a staple cartridge 26 and a firing means 28. An exemplary construction is illustrated in U.S. patent application Ser. No. 07/620,119, filed Nov. 30, 1990, now U.S. Pat. No. 5,129,570, issued Jul. 14, 1992, hereby incorporated by reference.

The upper frame 22 has an upper handle portion 30, an upper jaw portion 32 extending forwardly from the upper handle portion 30, and a latch pin 34 extending outwardly from opposite side faces of the upper jaw portion 32. The upper jaw portion 32 has in its inner surface an anvil portion 36 to close surgical staples which have penetrated through body tissues.

The lower frame 24 supports a lower jaw portion 38 projecting forwardly therefrom. The lower jaw portion 38 has an interior channel 40 into which the staple cartridge 26 is fitted and received.

A pivotal handle 42 is pivotally attached to the lower frame 24 so as to move between a release position and a locking position. The pivotal handle 42 includes a C-shaped hook member 44 having a locking cavity 46 for receiving the latch pin 34. When the pivotal handle 42 is moved to the release position as illustrated in FIG. 1, the hook member 44 is disengaged from the latch pin 34 so that the upper and lower frames 22, 24 may be separated from each other. As the pivotal handle 42 is moved toward the lower frame 24, the locking cavity 46 of the hook member 44 firmly receives the latch pin 34 in the locking position so that the upper and lower frames 22, 24 are locked together.

The lower frame 24 further includes a firing knob 48 movable along a longitudinally-extending guide slot 50 which is formed in a side wall of the lower frame 24.

As best illustrated in FIG. 2, the staple cartridge 26 has a body which includes opposite side walls 52 configured to be slidably received in the interior channel 40 of the lower jaw portion 38. The staple cartridge 26 further has at its rear end a pair of laterally spaced parallel projection arms 54 respectively extending downwardly from an underface of the staple cartridge 26. The projection arms 54 are designed to be received in an opening 56 (FIG. 3) formed in a bottom wall of the lower jaw portion 38.

The body of the staple cartridge 26 is laterally divided by a longitudinally-elongated center slot 58 which extends from a rear end of the staple cartridge 26 toward a front end thereof. There are disposed a plurality of staple openings 60 defined by the cartridge body along the elongated center slot 58 for mounting a plurality of staple drive members 62 respectively having at least one staple driving surface 64 in association with a surgical staple 66 (FIG. 3). In the illustrated embodiment, the staple openings 60 are arranged in three laterally spaced, staggered rows respectively on opposite sides of the elongated center slot 58.

Referring to FIGS. 1 and 2, the firing means 28 comprises a plurality of movable members, such as right and left sets of two parallel pusher bars 68. The right and left sets are designed to be positioned on opposite sides of the elongated center slot 58. Each of the pusher bars 68 has a rear end operatively connected to the firing knob 48 for longitudinal movement therewith, and a front end extending forwardly through guide slots 70, 72 respectively formed in a guide block 76, with the pusher bars 68 joined together for conjoint movement by a knife block 74. The front end of each pusher bar 68 is provided with a wedge-shaped tip which defines an inclined cam surface 78 for engaging the staple drive members 62 as the pusher bars 68 are longitudinally and forwardly moved.

The firing means 28 further comprises a knife support bar 80 which has a rear end connected to the knife block 74 and a front end extending forwardly from the knife block 74 in alignment with the elongated center slot 58 of the staple cartridge 26. The knife support bar 80 is slidably received in a central slot 82 formed in the guide block 76 and is supported by a leaf spring 84. An inclined knife blade 86 having a cutting edge is located at the front end of the knife support bar 80.

FIG. 3 illustrates the operation of the pusher bars 68 and the knife blade 86. When the firing knob 48 is manually advanced, the pusher bars 68 simultaneously move in the longitudinal direction along the guide slots 70, 72. As the pusher bars 68 enter the staple cartridge 26 and move therethrough, the cam surfaces 78 of the pusher bars 68 engage the staple drive members 62 within the body of the cartridge and transmit vertical or upward motion to the staple drive members 62. This causes the surgical staples 66 to be driven through the body tissues against the anvil portion 36 of the upper jaw portion 32, so that surgical staples 66 are formed in the tissues gripped between the upper and lower jaw portions 32, 38. The simultaneous longitudinal motion of the knife support bar 80 causes the knife blade 86 to follow, cutting the tissues between the parallel sets of three staple rows.

Figure 4:
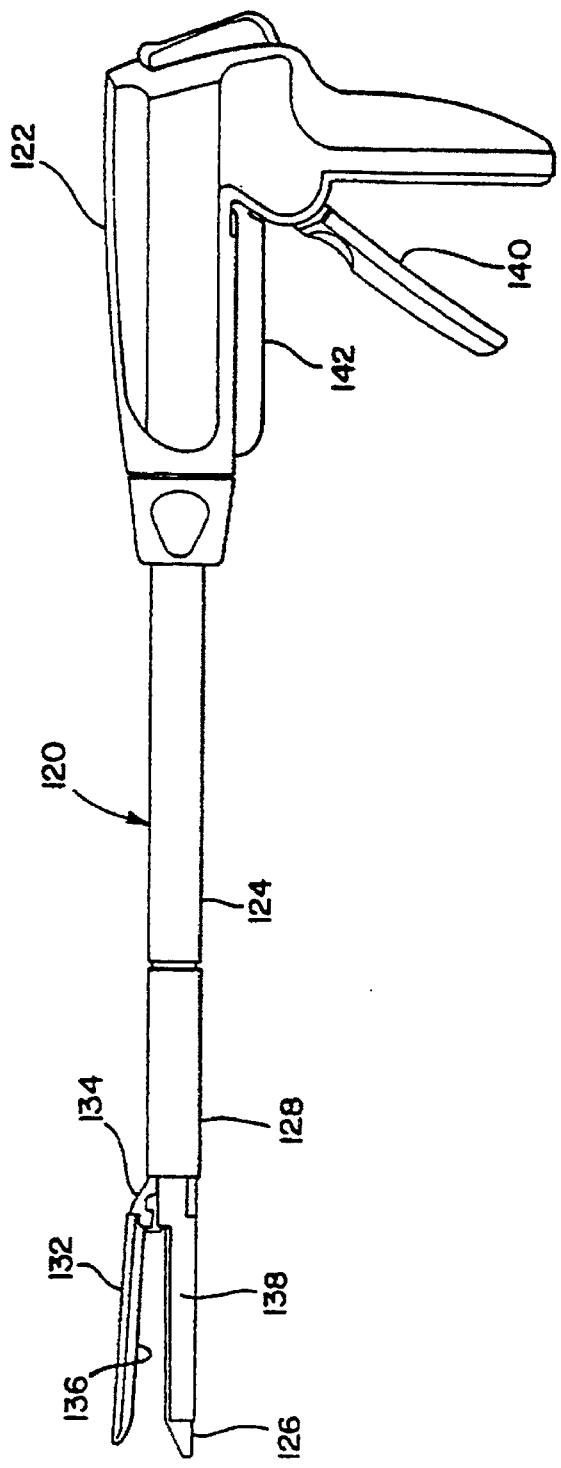
FIG. 4 is a side elevational view of an endoscopic surgical stapler mounting the staple cartridge in accordance with the present invention.

FIG. 4 illustrates another exemplary surgical stapler for endoscopic application, during which access to a body cavity is usually effected with the aid of a trocar tube (not shown). An exemplary construction is disclosed in U.S. patent application Ser. No. 07/917,636, filed Jul. 20, 1992, now U.S. Pat. No. 5,307,976, hereby incorporated by reference. An endoscopic surgical stapler 120 generally comprises a handle portion 122, a shaft portion 124, a closure sheath 128, an upper jaw portion 132 having an anvil portion 136 and a rear camming surface 134, a lower jaw portion 138, a staple cartridge 126 mounted in the lower jaw portion 138, a closure handle 140 and a firing handle 142.

The staple cartridge 126 is of essentially similar construction as the staple cartridge 26 of the first stapler embodiment shown in FIGS. 1 through 3, and includes a body within which are mounted a plurality of rows of staple drive members respectively having at least one staple driving surface in association with a surgical staple (not shown in FIG. 4). Similarly, the endoscopic surgical stapler 120 includes a firing means of essentially similar construction as the firing means 28 of the first stapler embodiment.

The operation of the closure handle 140 advances the closure sheath 128, which in turn cams the rear camming surface 134 of the upper jaw portion 132, so that the upper jaw portion 132 is closed toward the lower jaw portion 138 for grasping the body tissues therebetween. The firing handle 142 is operable to activate pusher bars which transmit a vertical motion to staple drive members so that surgical staples are driven into the body tissues grasped between the upper and lower jaw portions 132, 138.

Figure 5:
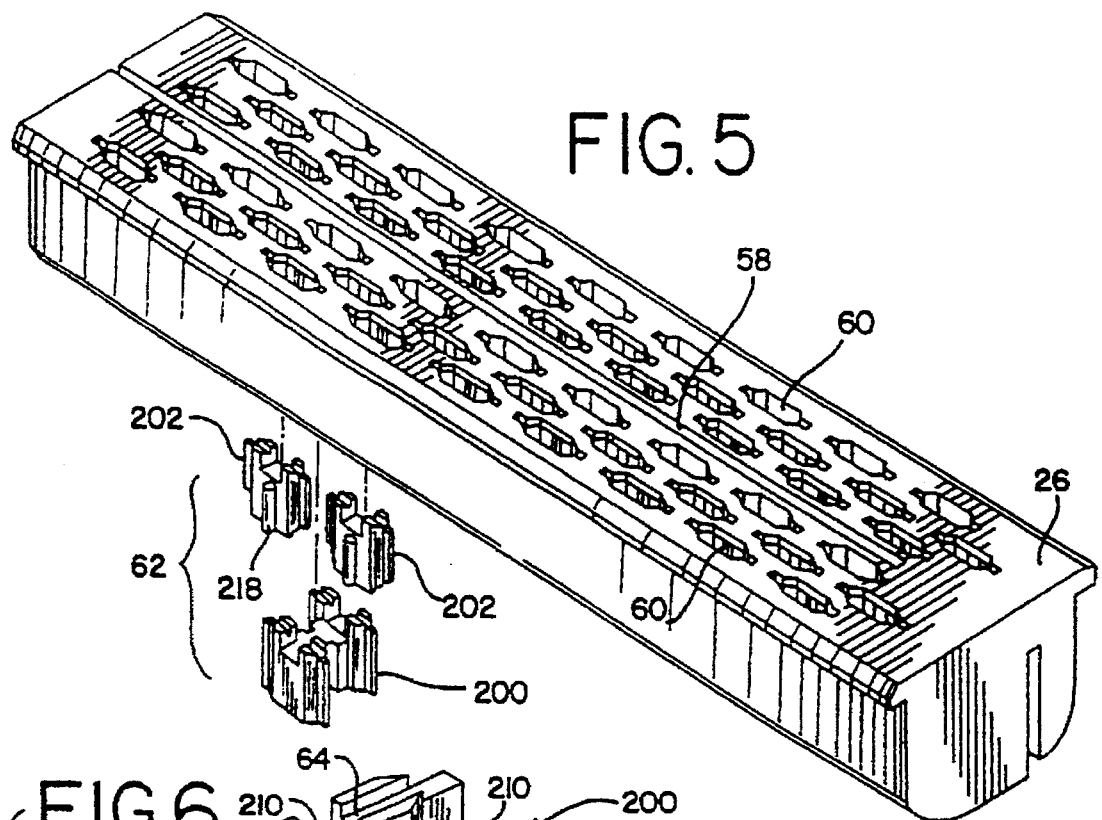
FIG. 5 is a perspective view of the staple cartridge, illustrating the first and second staple drive members in accordance with the present inventions.
Figure 6:
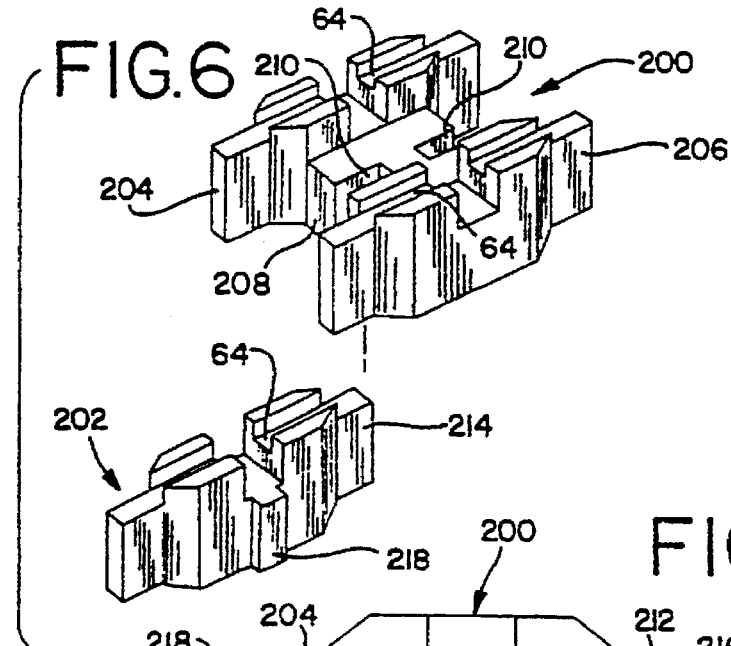
FIG. 6 is an enlarged perspective view of the first and second staple drive members.
Figure 7:
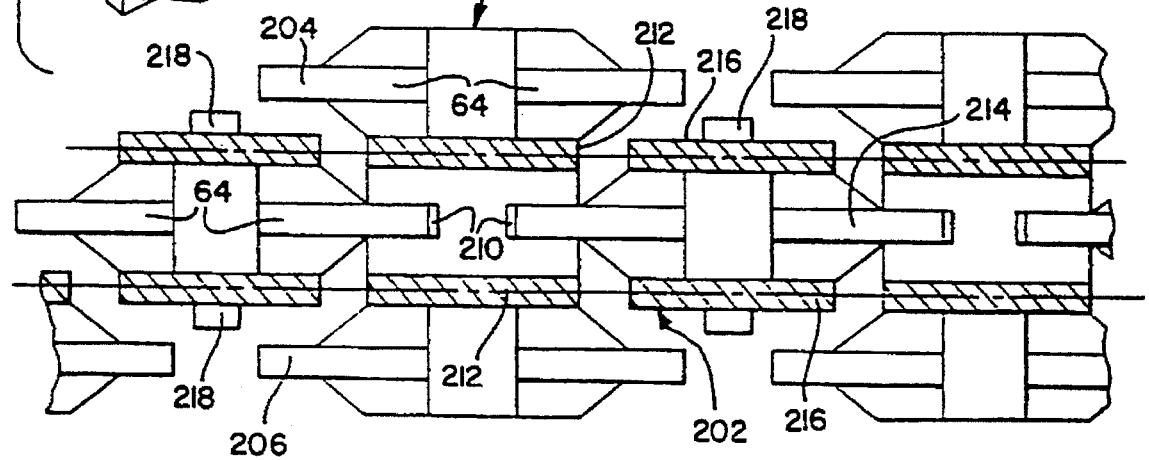
FIG. 7 is a diagrammatic view of the first and second staple drive members as mounted in the staple cartridge.

Referring now to FIGS. 5 through 7, the staple drive members 62 mounted in the staple cartridge 26 are illustrated. The staple cartridge 26 has three parallel rows of staple openings 60 defined by the body of the cartridge on each side of the longitudinally-elongated center slot 38. They are so arranged that staple openings 60 arranged in an outer row are laterally aligned to those in an inner row, but are staggered from those in a central row.

The staple drive members 62 include at least one pair of alternating first staple drive members 200 and second staple drive members 202 arranged in the longitudinal direction.

The first staple drive member 200 comprises a laterally spaced pair of plates 204, 206 each of which defines the longitudinally-extending staple driving surface 64 in association with the surgical staple 66, so that a laterally spaced pair of staple driving surfaces are provided. In this embodiment, the staple driving surfaces 64 of the first staple drive member 200 are illustrated to be parallel and laterally aligned with each other. The pair of plates 204, 206 respectively extend longitudinally between a proximal end and a distal end of the first staple drive member 200. The first staple drive member 200 further includes a laterally extending connecting portion 208 for connecting the laterally spaced pair of plates 204, 206. The longitudinal dimension of the connecting portion 208 is designed to be smaller than that of the first staple drive member 200, so that the first staple drive member 200 is configured to be generally H-shaped.

The connecting portion 208 may be integrally formed with the pair of plates 204, 206. The connecting portion 208 includes a pair of notches 210 formed at its opposite longitudinal ends. The pair of notches 210 are aligned with each other along a lateral centerline of the first staple drive member 200. The connecting portion 208 further includes one or more cam contact surfaces 212, preferably a pair of laterally spaced surfaces (exemplified in the embodiment of FIG. 7) positioned on opposite lateral sides of the lateral center line or of the longitudinally aligned notches 210. The cam contact surfaces are positioned for engagement by cam surfaces 78 of pusher bars 68, and may be inclined (see FIG. 3) in the direction of longitudinal movement of the pusher bars for camming cooperation therewith for driving staples.

The second staple drive member 202 includes a single plate 214 which extends longitudinally along a centerline of the second staple drive member 202 for defining distal and proximal ends of the second staple drive member 202, and the longitudinally-extending staple driving surface 64 in association with the surgical staple 66. The second staple drive member 202 further includes one or more cam contact surfaces, i.e., a pair of laterally spaced, longitudinally extending cam contact surfaces 216 disposed on opposite sides of the single plate 214. The second staple drive member 202 further includes lateral guide rails 218 designed to be guided by guide grooves formed in the body of the staple cartridge 26. The second staple drive member 202 is generally configured to be complementary to the H-shaped configuration of the first staple drive member 200 for positioning the staple driving surface 64 thereof in flanked relationship between the laterally spaced pair of the staple driving surfaces 64 of the first staple drive member 200.

In addition, the proximal and distal ends of the second staple drive member 202, including the plate 214, are respectively configured to be slidingly engageable with the respective first staple drive members 202 by sliding disposition in the notches 210, in tongue and groove relationship, so that the first and second staple drive members 200, 202 are slidable relative to each other when brought into engagement.

FIG. 7 is a diagrammatic view of the staple drive members as mounted in the body of the staple cartridge 26. In the illustrated embodiment, the staple drive members comprise alternating series of first and second staple drive members 200, 202, with each of the second staple drive members 202 being in sliding engagement with the adjacent first staple drive members 200. In such an arrangement, the staple driving surfaces 64 of the first and second staple drive members 200, 202 are longitudinally arranged in three parallel rows, and the cam contact surfaces 212, 216 of the first and second staple drive members 200, 202 are longitudinally arranged in two parallel rows. The number of the row(s) of the cam contact surfaces 212, 216 may be optionally reduced to one, or increased to three or more from two as illustrated in the embodiment of FIG. 7.

The sliding engagement of the first and second staple drive members 200, 202 enables individually guided movement therebetween, while substantially maintaining the structural and operational independence of each of the first staple drive members 200 from its adjacent second staple drive members 202. It has been observed that while the amount of force to drive the first staple drive member 200 is about twice the force required to drive the second staple drive member 202, the driving force required for each of the members is substantially less than arrangements wherein a drive member simultaneously drives three staples. It is believed that this substantially reduced force requirement provides a smoother and easier stapling operation.

Figure 8:
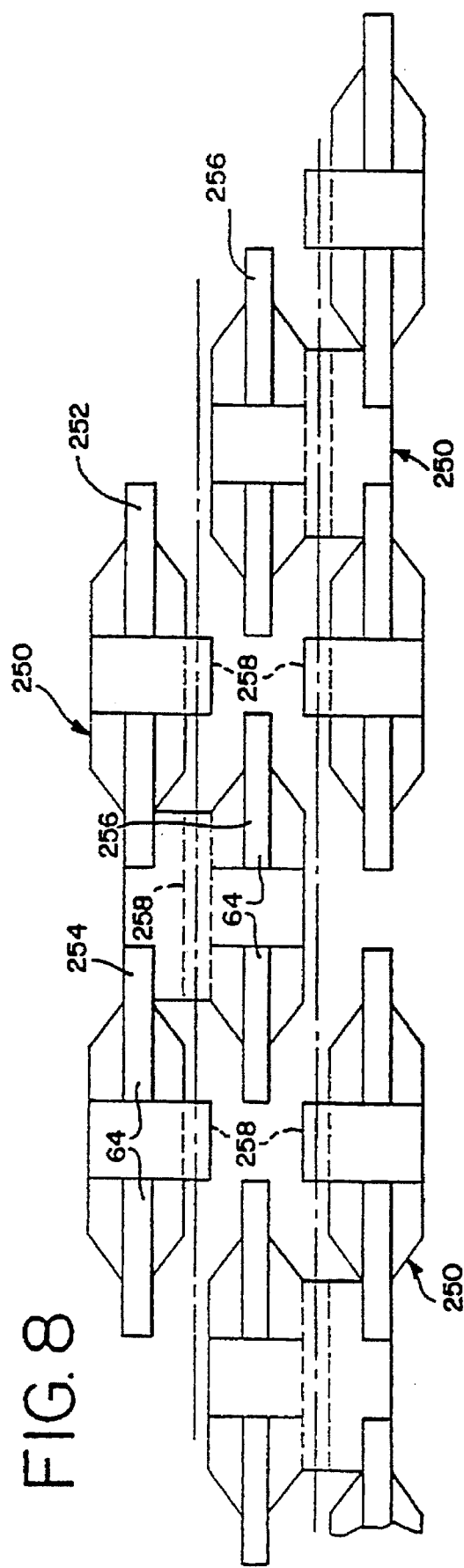
FIG. 8 and FIG. 8a are diagrammatic views of the three staple drive members in accordance with an alternative embodiment of the present invention as mounted in the staple cartridge.

FIG. 8 diagrammatically illustrates another embodiment of the staple driver members and one arrangement thereof within the body of cartridge 26. The staple drive members comprise a plurality of three staple drive members 250 longitudinally arranged in two staggered rows. Each of the three staple drive members 250 is configured to include staple drive plates similar to those of members 200, 202, with each member 250 comprising a front plate 252, a rear plate 254 longitudinally spaced from and aligned with the front plate 252, and a center plate 256 laterally spaced from and disposed longitudinally intermediate the first and second staple drive members 250, 252. Each of the plates 252, 254, 256 defines a longitudinally extending staple driving surface 64 in association with a surgical staple. The three staple drive member 250 further comprises a cam contact surface 258 longitudinally extending between the center plate 256 and the front plate 252 or the rear plate 254. As in the previous embodiment, members 250 are slidably disposed in the body of the cartridge 26 for movement in response to pusher bars of the stapler.

In the illustrated embodiment, longitudinally adjacent ones of the three staple drive members 250 are arranged in a laterally-reversed or inverted orientation and configured to be complementary to each other. The respective center plates 256 of adjacent three staple drive members 250 are disposed in longitudinal alignment with each other, so that the staple driving surfaces thereof are arranged in three laterally spaced rows, and the cam contact surfaces thereof are arranged in two laterally spaced rows.

Figure 8A:
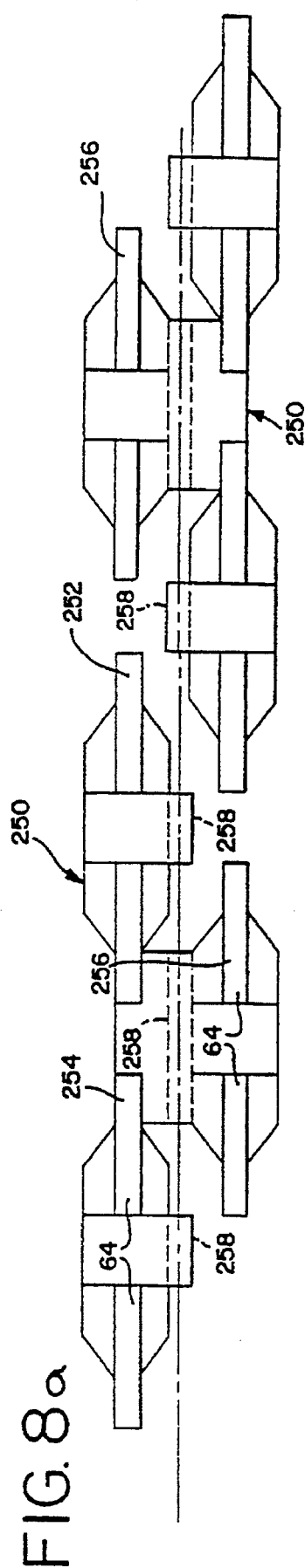

Alternatively, the three staple drive members 250 may be arranged such that the center plate 256 of one of the three staple drive members 250 is longitudinally aligned with the front and rear plates 252, 254 of its longitudinally adjacent three staple drive members 250. In such an arrangement (see FIG. 8a), the staple driving surfaces of the adjacent three staple drive members 250 are arranged in two laterally spaced rows, and the cam contact surfaces thereof are arranged in a single row.

Referring now to FIGS. 9–11, therein is illustrated a spine-like flexible drive element 300 for providing a continuous cam contact surface 302 in operative association with a plurality of longitudinally arranged staple drive members. The provision of such flexible drive element 300 facilitates a smooth stapling operation as the drive members are progressively driven by the pusher bars of the stapler.

In the embodiment of FIG. 9, the flexible drive element 300 has a continuous base 304 extending in the direction of movement of the cam surface for providing the cam contact surface 302 for engagement by the cam surface, such as of the pusher bar. The alternating series of the first and second staple drive members 200, 202, as illustrated in FIGS. 5 through 7, are positioned in operative association with the flexible drive element 300, so that the longitudinal movement of the cam surface of the pusher bar on the cam contact surface 302 of the flexible drive element 300 effects a sequential, progressive pushing of the first and second staple drive members 200, 202.

At least some of the staple drive members, such as the first and/or second staple drive members 200, 202 may be releasably retained by the flexible drive element 300. This can be achieved by fitting the drive element 300 into suitable grooves defined by the drive members 200, 202 generally at the cam contact surfaces thereof. Additionally, at least some of the staple drive members, such as alternative ones of the staple drive members, e.g. first or second staple drive members 200, 202, may be integrally connected to the flexible drive element 300. For example, the second staple drive members 202 (each having a single staple driving surface 64) may be integrally connected to the flexible drive element 300 (either by formation therewith, or by suitable bonding). This arrangement permits the first staple drive members 200 to be releasably retained and mounted between the second drive members 202 on the drive element 300, thus facilitating assembly of the components in the body of the cartridge, and subsequently retaining the drive member in position with the staple cartridge.

In the illustrated embodiment, the first staple drive member 200 has a longitudinally extending slot or channel 306 for receiving the flexible drive element 300 at its lower surface opposite the staple driving surfaces. The flexible drive element 300 includes laterally spaced guide ridges 308 respectively longitudinally extending along opposite lateral edges of the flexible drive element 300 for guiding the longitudinal movement of the cam surface 78 of the pusher bar 68 thereon.

Each of the guide ridges 308 may be generally discontinuous and comprise a series of first and second guide ridge portions 310, 312 disposed at longitudinal intervals, as shown in FIG. 9, to allow the flexible drive element 300 to flex with low resistance, while guiding the longitudinal movement of the cam surface 78 of the pusher bar 68. The laterally spaced pair of first guide ridge portions 310 are configured to be slidably resiliently received in the channel 306 of the first staple drive member 200 for releasably retaining the first staple drive member 200. Each of the laterally spaced pairs of second guide ridge portions 312 is formed to have a cross-sectional shape substantially registered with that of the guide rails of the second staple drive member 202 so that second guide ridge portion 312 and the guide rail 218 are together guided by the guide groove formed in the body of the staple cartridge 26.

Alternatively, each of the guide ridges 308 may comprise a continuous flange as shown in FIGS. 10–12. The continuous flange has an undulated surface portion, such as an undulated lower surface 314 to allow the continuous flange to flex with low resistance while better guiding the longitudinal movement of the cam surface 78 of the pusher bar 68.

As best seen from FIGS. 11 and 12, the continuous surface 302 of the flexible drive element 300 includes an inclined surface portion, such as an inclined starting ramp surface 316 for engageably receiving the cam surface 78 of the pusher bar 68. The inclined starting ramp surface 316 may be formed by angularly orientating a longitudinal end portion 318 of the flexible drive element 300. In the illustrated embodiment, the guide ridges 308 are not provided on the longitudinal end portion 318 in order to provide the longitudinal end portion 318 with desired flexibility to smoothly receive the cam surface 78.

An outer edge 320 of the longitudinal end portion 318 may be attached to the body of the staple cartridge 26. Alternatively, the longitudinal end portion 318 may be at least partly attached or connected to an inclined surface formed in the endmost first or second staple drive member 200, 202. Such an inclined surface, for example, may be formed in the channel 306 of the first staple drive member 200.

When the pusher bar 68 advances in the longitudinal direction, the cam surface 78 of the pusher bar 68 rides on and engages the inclined ramp surface 316 of the flexible drive element 300. Due to the flexible nature of the flexible drive element 300, continued engagement by the cam surface 78 as the pusher bar 68 further advances thereon and subsequently sequentially pushes or drives the staple drive members 200, 202 upwardly in the cartridge body. In accordance with this structure, the provision of cam contact surfaces 212, 216 on each of the staple drive members 200, 202 may be omitted since the pusher bar does not directly engage and contact the drive members.

Figure 13:
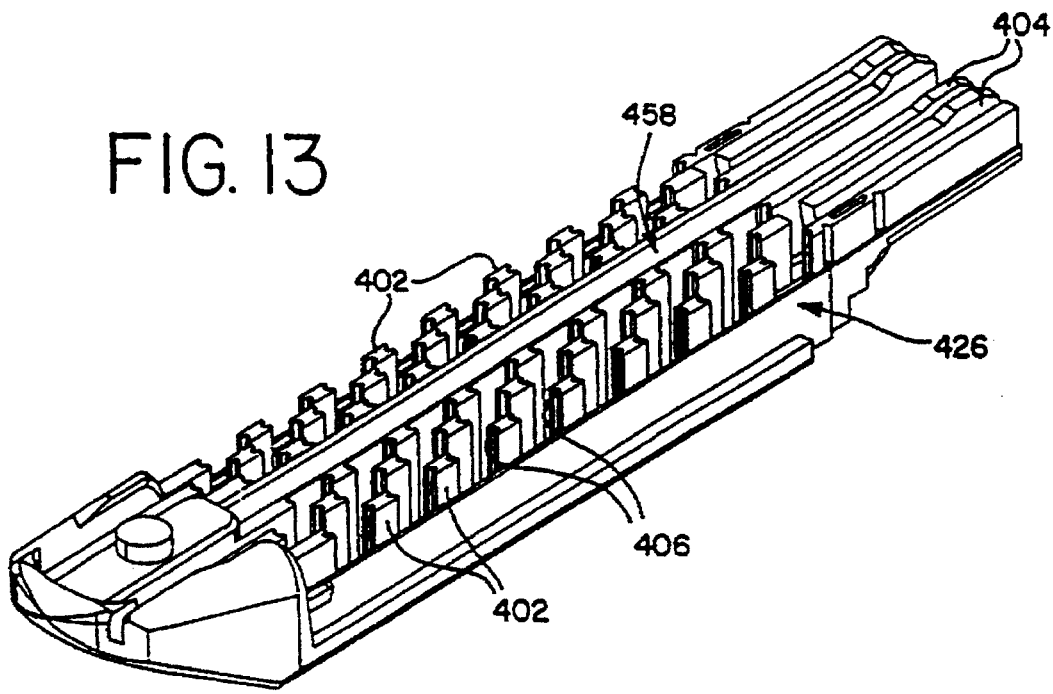
FIG. 13 is a perspective view of a staple cartridge body of a further embodiment of the present invention.

FIGS. 13 through 16 illustrate still another embodiment of a surgical stapler which comprises a staple cartridge having a cartridge body 426 for carrying a plurality of staple drive members. The illustrated embodiment shows one exemplified arrangement of those staple drive members within the body of the cartridge 426. The cartridge body 426 as illustrated in FIG. 13 includes an elongated center slot 458 which slidably receives a knife support bar (not shown). A plurality of uprights 402 integrally formed with the cartridge body 426 are arranged in three laterally spaced, staggered rows respectively on opposite sides of the elongated center slot 458. Specifically, they are arranged such that the uprights 402 in an outer row are laterally aligned with those in an inner row, but are staggered from those in a central row. A pusher bar slot 404 is defined between the respective laterally spaced, adjacent rows of uprights 402 for slidably receiving a pusher bar 468 (see FIGS. 15 and 16). Each of the uprights 402 has notches at its longitudinal opposite ends for defining vertically extending guide grooves 406.

Figure 14:
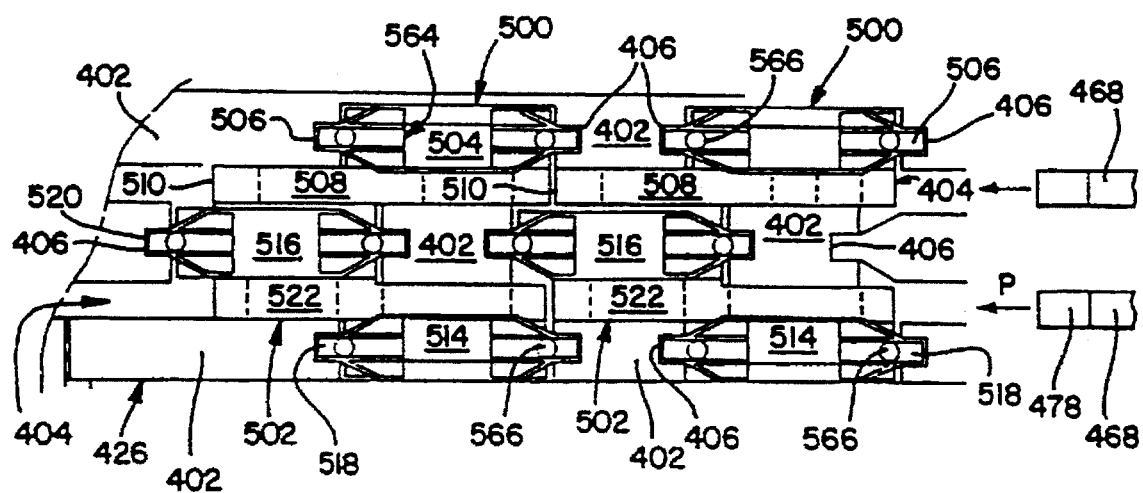
FIG. 14 is a diagrammatic view of single and double staple drive members of the further embodiment of the present invention in the cartridge body of FIG. 13.

Referring to FIG. 14, the staple drive members mounted within the cartridge body 426 comprise single staple drive members 500 and double staple drive members 502. Each of the single staple drive members 500 comprises a single plate 504 configured to extend longitudinally between the longitudinally adjacent uprights 402. The single plate 504 has guide rails 506 at its front and rear ends for being vertically slidably guided by longitudinally confronting guide grooves 406 of the longitudinally adjacent uprights 402 in the inner row. The single plate 504 further has a longitudinally extending staple driving surface 564 in association with a surgical staple 566. The single staple drive member 500 further comprises a body portion 508 which defines a distal end 510 extending along the pusher bar slot 404 within the cartridge body 426 beyond the front end of the single plate 504. In the embodiment of FIG. 14, the body portion 508 of one (right) of the single staple drive members 500 (the right-hand one in FIG. 14) is shown to extend longitudinally so that the distal end 510 positions coterminous to a front end of the upright 402 whose rear end has the guide groove 406 to vertically guide the front end of the single plate 504. The body portion 508 is provided with one or more cam contact surfaces 512 for engagement by one or more cam surfaces 478 of the pusher bars 468.

Each of the double staple drive members 502 comprises a pair of laterally spaced, and longitudinally staggered, first and second plates 514, 516. The first plate 514 has guide rails 518 at its front and rear ends for being vertically slidably guided by guide grooves 406 on uprights 402 in the outer row. The second plate 516 is disposed laterally forwardly of the first plate 514, and has guide rails 520 at its front and rear ends for being vertically slidably guided by guide grooves 406 on uprights 402 in the central row. Each of the first and second plates 514, 516 defines a longitudinally-extending staple driving surface 564 in association with the surgical staple 566. The double staple drive member 502 further comprises a connecting portion 522 which longitudinally extends along the pusher bar slot 404 within the cartridge body 426, and connects the first and second plates 514, 516. The connecting portion 522 is laterally dimensioned and configured so that it is vertically slidably guided in the pusher bar slot 404. The connecting portion 522 includes one or more cam contact surfaces 524, such as inclined undersurfaces (FIG. 15), for engagement by one or more cam surfaces 478 of pusher bars 468.

In the embodiment of FIG. 14, the single staple drive members 500 and the double staple drive members 502 are arranged within the cartridge body 426 such that the single plate 504 of the respective single staple drive member 500 is laterally aligned with the first plate 514 of the respective double staple drive member 502. The body portion 508 of the single staple drive member 500 and the connecting portion 520 of the double staple drive member 502 are dimensioned to have substantially the same length, and the respective body portion 508 and connecting portion 520 are laterally aligned with each other within the cartridge body 426.

With such a construction, as the pusher bars 468 advance in the longitudinal direction P as indicated by arrows in FIG. 14, the respective cam surfaces 478 of the pusher bars 468 sequentially engage and drive the single staple drive members 500 and the double staple drive members 502, so that three parallel sets of the surgical staples are fired and placed in body tissues.

Figure 15:
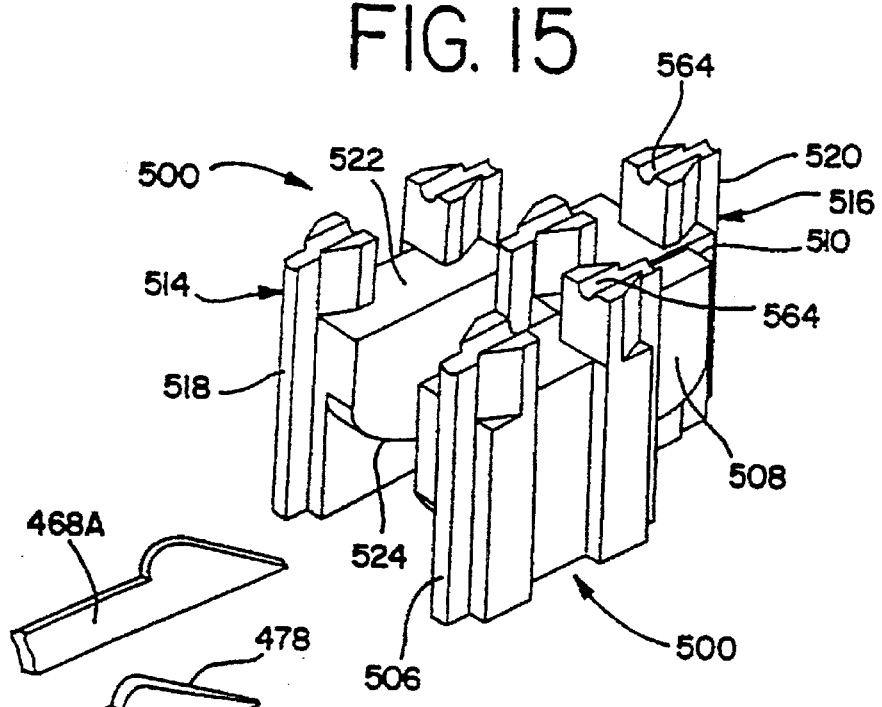
FIGS. 15 and 16 are perspective views of the single and double drive members of the further embodiment of the present invention.
Figure 16:
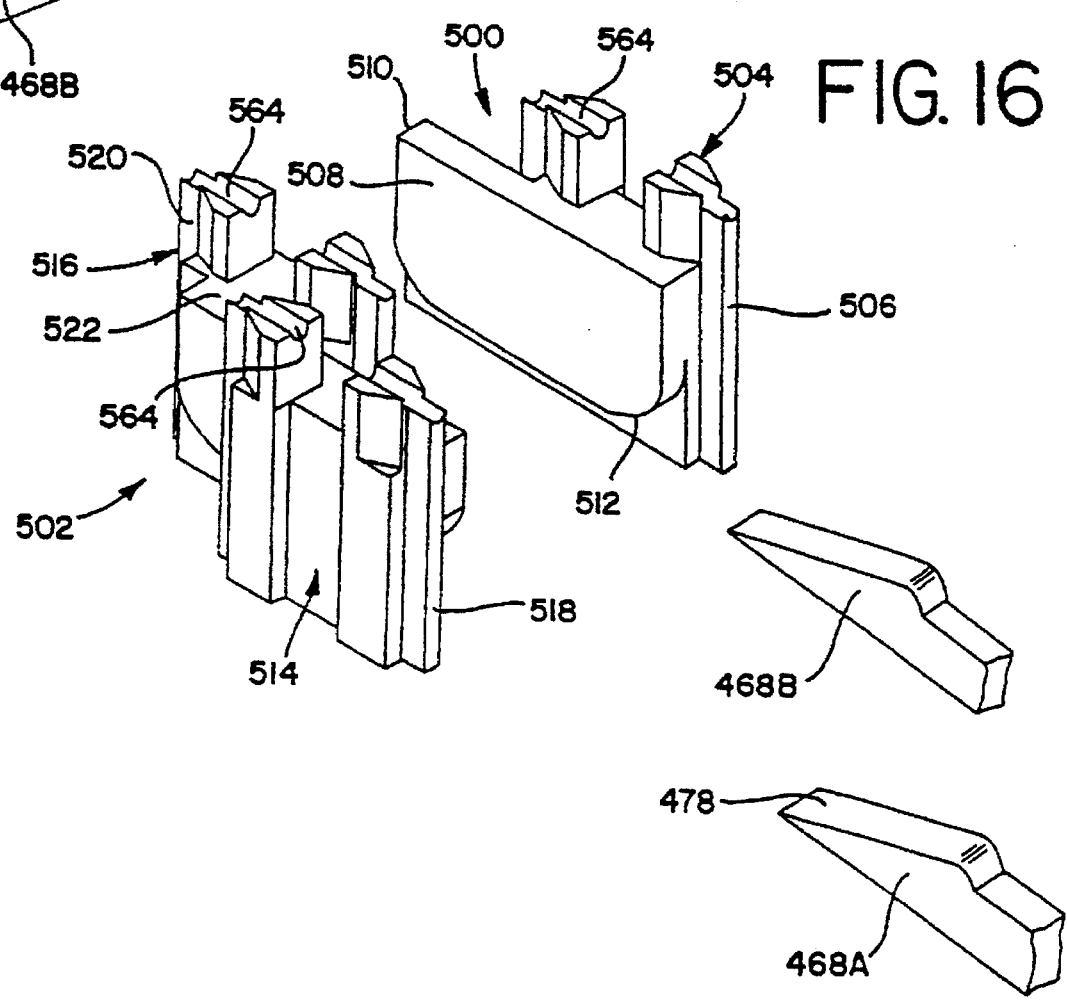

As illustrated in FIGS. 15 and 16, the inclined cam surface 478 of one of the pair of pusher bars 468A or 468B is positioned forwardly of the other pusher bar 468B or 468A, so that a staggered or delayed camming action by the pair of the pusher bars 468A, 468B effects distribution of the force to drive the single and double staple drive members 500, 502. Due to such distribution of the driving force in driving three parallel surgical staples 566, substantially less force is required for the present arrangement, wherein the respective single and double drive members 500, 502 sequentially drives three parallel surgical staples 566, than arrangements wherein one or more drive members simultaneously drive three parallel staples. This substantially reduced force requirement provides a smoother and easier stapling operation. Such staggering of the cam surfaces can be provided not only on each side of the knife slot, but also by staggering the wedges on one side of the slit with respect to the one or more wedges on the other side of the slot.

An additional feature of this embodiment relates to the manner in which the body portion 508 of each single staple drive member 500 is laterally offset with respect to the single plate 504 thereof. By this arrangement, uprights 402 can act along a relatively large extent of the height of each single drive member for guiding the movement thereof, since the associated wedge passes along the side of each upright 402. This desirably serves to prevent cocking or jamming of the single drive member as it is acted upon and driven by the associated wedge, and additionally desirably acts to guide and confine the legs of the staple as it is driven (the uprights 402 provide this staple guiding action for all of the staples of the cartridge). Without such a lateral offset of the cam-engaging surface of the driver, the required clearance for advancement of the wedge would not permit the driver to be supported and guided along as great an extent of its vertical surface which faces in the direction in which the wedges are being advanced. Without such support, cocking of the drive member can be more likely, with engagement by the wedge inducing rotational movement in the driver.

From the foregoing, it will be observed that numerous modifications and variations can be effected without departing from the true spirit and scope of the novel concept of the present invention. It is to be understood that no limitation with respect to the specific embodiments illustrated herein is intended or should be inferred. The disclosure is intended to cover by the appended claims all such modifications as fall within the scope of the claims.

What is claimed is:
1. A surgical stapler comprising:
cam means having a cam surface;
means for actuating said cam means for a longitudinal movement of said cam surface;
a staple cartridge including a plurality of staple drive members longitudinally arranged and driven by the longitudinal movement of said cam surface, said staple drive members each having three staple driving surfaces, each said staple driving surface being engageable with a surgical staple, said three staple driving surfaces comprising a front staple driving surface and a rear staple driving surface longitudinally aligned with each other and a center staple driving surface laterally spaced from said front staple driving surface and said rear driving surface; and
at least one longitudinally extending cam contact surface formed in each of said staple drive members, said cam contact surface being laterally spaced from each of said front, rear and center staple driving surfaces, said cam contact surface being positioned laterally between said center staple driving surface and said front and rear staple driving surfaces, and in longitudinal alignment with said center staple driving surface,
longitudinally adjacent ones of said staple drive members being arranged in a laterally-reversed orientation and configured to be complementary to each other so that said front, rear and center staple driving surfaces of said staple drive members are arranged in at least two laterally spaced rows and said cam contact surfaces of said staple drive members are arranged in one or more rows laterally spaced from said rows of staple driving surfaces.

2. The surgical stapler of claim 1, wherein
said center staple driving surfaces of said adjacent drive members are longitudinally aligned with each other so that said front, rear and center staple driving surfaces of said drive members are arranged in three laterally spaced rows.

3. The surgical stapler of claim 1, wherein
said center staple driving surface of any one of said drive members is longitudinally aligned with said front and rear driving surfaces of an adjacent staple drive member so that said from, rear and center staple driving surfaces of said drive members are arranged in two laterally spaced rows.

* * * * *

UNITED STATES PATENT AND TRADEMARK OFFICE
CERTIFICATE OF CORRECTION

PATENT NO.   : 5,630,541
DATED        : May 20, 1997
INVENTOR(S)  : Williamson IV et al.

It is certified that error appears in the above-indentified patent and that said Letters Patent is hereby corrected as shown below:

```
In the claims

Column 12, line 43, "from" should be "front".
```

Signed and Sealed this

Twenty-eighth Day of October, 1997

Attest:

BRUCE LEHMAN

Attesting Officer

Commissioner of Patents and Trademarks